United States Patent [19]
Guignard

[11] Patent Number: 5,411,517
[45] Date of Patent: May 2, 1995

[54] CANNULA FOR USE DURING ARTHROSCOPIC PROCEDURES

[76] Inventor: Mireille Guignard, "Le Vezely" Sergy Gare, F-01630 Saint-Genis/Pouilly, France

[21] Appl. No.: 157,021
[22] PCT Filed: Mar. 31, 1993
[86] PCT No.: PCT/EP93/00792
 § 371 Date: Dec. 1, 1993
 § 102(e) Date: Dec. 1, 1993
[87] PCT Pub. No.: WO93/19790
 PCT Pub. Date: Oct. 14, 1993

[30] Foreign Application Priority Data
Apr. 2, 1992 [FR] France ............... 92 04149

[51] Int. Cl.⁶ .............................. A61M 29/00
[52] U.S. Cl. ................... 606/198; 604/104; 604/267
[58] Field of Search ............ 606/198; 604/15, 16, 604/33, 104–109, 249, 267

[56] References Cited
U.S. PATENT DOCUMENTS

| 765,879 | 7/1904 | Campbell | 606/198 |
| 1,637,264 | 7/1927 | Masonick et al. | 604/107 |
| 1,827,497 | 10/1931 | Varney | 606/198 |
| 2,042,900 | 6/1936 | James | 604/106 |
| 2,201,749 | 5/1940 | Vandegrift | 604/107 |
| 2,541,691 | 2/1951 | Eicher | . |
| 4,692,153 | 9/1987 | Berlin et al. | . |

FOREIGN PATENT DOCUMENTS

| 2321902 | 3/1977 | France | . |
| 0073751 | 9/1917 | Germany | 606/198 |

*Primary Examiner*—C. Fred Rosenbaum
*Assistant Examiner*—Perry E. Van Over
*Attorney, Agent, or Firm*—Cushman, Darby & Cushman

[57] ABSTRACT

A cannula comprising a tubular element with two longitudinal slots lying in a diametral plane and defining two blades joined at the ends thereof by a block of material. A plunger with a tapering tip is linked to a contol rod and a grip and extends through a passage and into a channel in the tubular element, which channel ends behind the free ends of the blades. When the plunger is driven towards the free end of the tubular element, its conical portion reached the end of the channel and pushes the blades apart laterally so that the block of material breaks and allows said blades to spread apart.

6 Claims, 1 Drawing Sheet

CANNULA FOR USE DURING ARTHROSCOPIC PROCEDURES

The present invention relates to a cannula for evacuating a rinsing liquid during an endoscopic operation or examination.

It is well known that the good progress of surgical endoscopic operations, and more particularly arthroscopies by irrigation under constant pressure of physiological serum through an arthroscope, is associated with good circulation of the liquid that rinses the arthroscope through the cannula, which by continuously eliminating debris or blood lends transparency and guarantees visibility in the operation cavity. If this circulation ceases, because the evacuation cannula that is connected to suction becomes plugged, then the operative field becomes opaque virtually immediately.

In arthroscopy of the knee, the position of the suction cannula is preferably within a zone of the joint capsule where the visual field of the camera and the surgical instruments are not located, so as not to impede the movements of the surgeon's hands as he works, nor reduce the visual field. As a result, the zone most often used for placement of the cannula is the subquadricipital cul-de-sac. Given its position, the cannula is frequently isolated from the irrigation zone, in certain positions of the knee.

Under these particular conditions, and depending on the size of the synovial, it may happen that the irrigating liquid will not be able to move from the pouch where the arthroscope is located to that where the cannula is located. At that moment, the circulation that enables the rinsing is interrupted; the liquid rapidly becomes turbid and makes the operative field opaque, thus preventing any operation.

The present invention proposes to overcome this disadvantage, at least in part.

To that end, the subject of this invention is a cannula for evacuating a rinsing liquid during an endoscopic, and in particular arthroscopic, operation or examination, characterized in that it includes a tubular element that at least in part forms an evacuation conduit for the rinsing liquid; at least two lateral elongated slots made on either side of the portion of the evacuation conduit formed by the tubular element, beginning at one free end of this tubular element and extending over a portion of its length, forming two small tongues solid with this tubular element; a passage for connecting the conduit to the outside of the cannula; a spacer device for exerting forces upon the small tongues that tend to space the tongues apart on either side of the slot; means for controlling the spacer device that are capable of being maneuvered from outside the conduit through the passage; and sealing means for enabling the sealed passage of the control means from the exterior of the cannula to the spacer device, at least in the spaced-apart position of the small tongues.

The main advantage of the invention is due to the fact that the cannula acts as a spacer when it is introduced into the subquadricipital cul-de-sac. It thus keeps the joint capsule open, to enable good circulation of the liquid through the cavity between the entry of this liquid at the level of the arthroscope and its exit at the level of the cannula.

Further advantages will become more apparent from the ensuing description and from the accompanying drawings, which schematically and by way of example illustrate an embodiment of the cannula that the subject of the invention.

Figure 3:
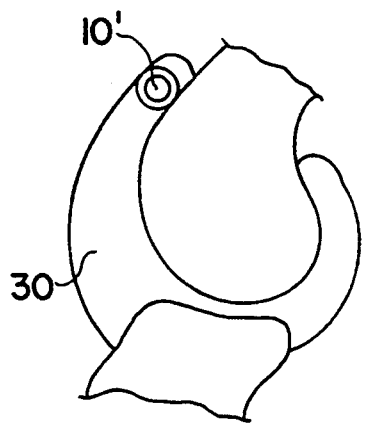
FIG. 3 is a lateral view of a knee in a position of extension, with a cannula of the prior art, seen in section.
Figure 4:
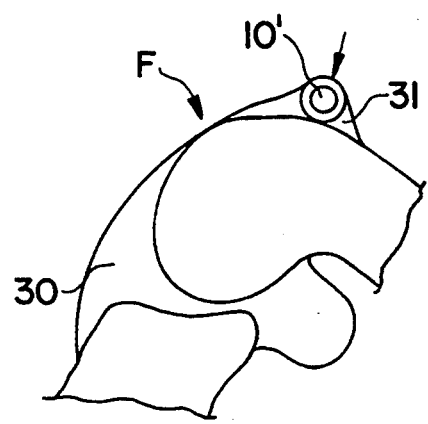
FIG. 4 is a lateral view of the same knee in the position of flexion.

FIGS. 3 and 4 show a knee in which a cannula 10' can be seen, inserted into the anterior subquadricipital cul-de-sac 31; the operating zone is identified by reference numeral 30. As can be seen, when the cannula communicates with the operating zone 30 when the knee is in extension (FIG. 3), the communication is interrupted in the region of the arrow F when it is in flexion, such that the rinsing liquid introduced through the arthroscope (not shown) and located in the operating zone 30 can no longer be evacuated through the cannula 10' located through the zone 31. The pump that supplies the arthroscope is provided with an automatic pressure control; hence it shuts off, and the liquid, no longer circulating, rapidly becomes turbid.

Figure 1:
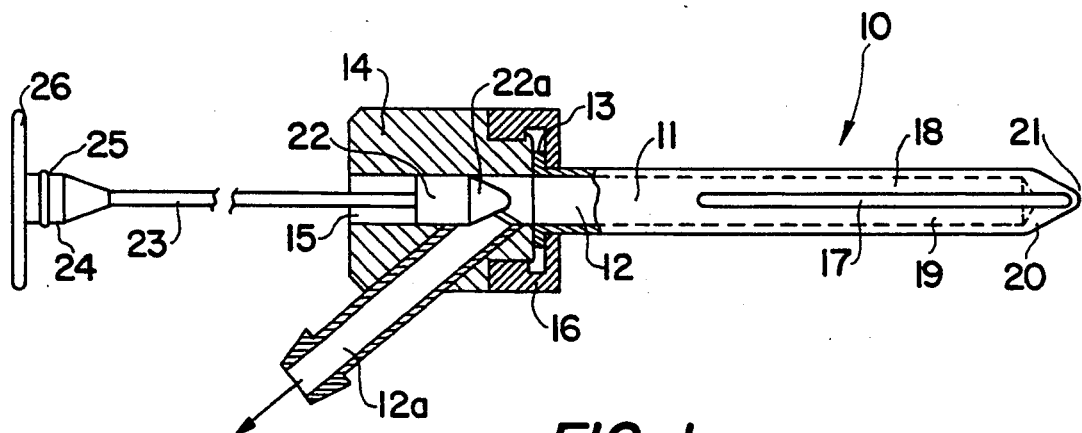
FIG. 1 is a lateral elevation view in partial section, of this cannula in a first working position.
Figure 2:
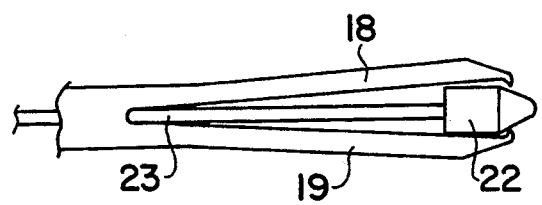
FIG. 2 is a fragmentary view of FIG. 1, in a second position.

The cannula 10 that is the subject of the invention, illustrated by FIGS. 1 and 2, includes a tubular element 11 whose internal conduit 12 serves as an evacuating conduit. This tubular element 10 has a small collar 13 on one end, which enables it to be fixed detachably on a connection element 14 between a conduit 12a, forming an elbow that is inclined relative to the axis of the conduit 12 and is intended to be connected to a suction pump (not shown), and a passage 15 that extends coaxially with the conduit 12. A fixation ring 16, screwed to the connection element 14, presses the small collar 13 against one face of this element 14, the face into which one end of the passage 15 discharges. Sealing means (not shown), are provided in order to make the fixation of the tubular element 11 on the connection element 14 leakproof.

The tubular element 11 includes two slots 17 extending within the same diametral plane and thus forming two small tongues 18 and 19 on either side of the conduit 12. This conduit comes to an end before the conical end 20 of this element, and an islet of material 21 is reserved so as to form a link between the respective ends of these small tongues. Preferably, this tubular element 11 is of plastic, particularly PVC.

A piston 22, terminated by a conical spacer end 22a, or spacer means is engaged in the passage 15. The rear end of this piston is solid with a maneuvering rod 23 that terminates in a second piston 24 provided with an O-ring seal 25 defining sealing means. A grasping device 26, solid with the piston 24, serves to actuate the piston rod 22 in its conical spacer end 22a.

When the cannula 10, shown in FIG. 1, is put in place for the sake of the operation, for example in the position shown in FIGS. 3 and 4, the tubular element 11 is first introduced into the appropriate cavity. Next, the piston 22 is pushed forward: Its conical end 22a meets a resistance as it arrives at the end of the conduit 12 adjacent to the free end of the tubular element. At that moment, the connection element 14 is held with one hand, and with the other hand one pushes the grasping device 26. The force thus developed by the cone 22a on the free ends of the small tongues 18, 19 breaks the link formed by the islet of plastic material 21 and thus makes it possible to space the small tongues 18, 19 apart from one another, as illustrated by FIG. 2. Spacing the small tongues 18 and 29 apart in this way makes it possible to act upon the wall of the subquadricipital pouch by distancing it from the joint, in order to reestablish the link between the zones 30 and 31 in the flexion position of the knee. In the anterior end position of the piston 22 shown in FIG. 2, the piston 24 and its O-ring 25 are adjusted in the passage 15 and thus assure tightness, such that the evacuation of the rising liquid takes place through the conduit 12a, which is preferably inclined with respect to the common axis of the passage 15 and the conduit 12.

If in the position shown in FIG. 2 the evacuation conduit 12 becomes plugged up by obstruction with a solid body, it suffices to withdraw the piston 22 to the rear, by pulling on the grasping device 26, in order to remove the body from the conduit and then return the piston 22 to its position in which it spaces the small tongues 18 and 19 apart, by pushing on the grasping device 26 again.

It is understood that the solution shown is one possible exemplary embodiment of the invention, and other means may also be used, in particular for spacing the small tongues 18 and 19 apart. Hence it is possible to conceive of replacing the piston 22 with an inflatable balloon and the rod 23 with a feed conduit, one end of which would open into the interior of the balloon and the other end of which could for example be connected to a manually or pedal-actuated blower in order to inflate the spacer element so as to space the tongues 18 and 19 apart from one another. In addition, the number of tongues 18 and 19 could be greater than 2, for example being 3 or 4.

I claim:

1. A cannula for evacuating a rinsing liquid during an arthroscopic operation or examination comprising:

a tubular element that at least in part forms an evacuation conduit for said rinsing liquid; at least two lateral elongated slots made on either side of the evacuation conduit formed by said tubular element, beginning at one free end of the tubular element and extending over a portion of its length, forming two small tongues solid with the tubular element;

a passage for connecting said conduit to the outside;

spacer means, extendable into said passage for exerting forces upon said small tongues that tend to space the tongues apart on either side of said slots;

means for controlling said spacer means so that said spacer means can be maneuvered from outside said conduit and slidably moved through said passage; and sealing means cooperating with said passage for sealing said passage when said spacer means is in a position spacing the tongues apart, wherein the cross-section of said conduit is reduced in the vicinity of free ends of said tongues, said spacer means comprises a piston slidingly fitted into said conduit and said control means comprises a rod solid with a rear end of said piston and so providing a larger section of said conduit and a step between the piston and the rod so that said rod is able to slide the piston (1) in a forward direction into the reduced cross-section of said conduit, spacing the tongues apart and (2) in a rearward direction to clear said conduit of any obstruction.

2. The cannula of claim 1 wherein said tubular element is detachably mounted on an element for connection between said conduit and said passage.

3. The cannula of claim 2, wherein said tubular element and said passage are coaxial.

4. The cannula of claim 1 wherein the end of said rod opposite an end that is solid with said spacer means terminates in a maneuvering device and in a piston surface associated with said sealing means, said sealing means including an O-ring.

5. The cannula of claim 1, wherein linking means that can be broken by the force generated by said spacer means join free ends of said tongues to one another.

6. The cannula of claim 5, wherein said tubular element is of plastic material, and the linking means are formed by at least one islet of material included between said free ends of the tongue.

* * * * *